US006492125B2

(12) United States Patent
Kauvar et al.

(10) Patent No.: US 6,492,125 B2
(45) Date of Patent: Dec. 10, 2002

(54) METHOD TO ASSESS LIBRARY X LIBRARY INTERACTIONS

(75) Inventors: Lawrence M. Kauvar, San Francisco, CA (US); John Sedat, San Francisco, CA (US)

(73) Assignee: Trellis Bioscience, Inc., Mountain View, CA (US)

( * ) Notice: Subject to any disclaimer, the term of this patent is extended or adjusted under 35 U.S.C. 154(b) by 0 days.

(21) Appl. No.: 09/332,613

(22) Filed: Jun. 14, 1999

(65) Prior Publication Data
US 2001/0044116 A1 Nov. 22, 2001

Related U.S. Application Data

(63) Continuation-in-part of application No. 09/146,984, filed on Sep. 3, 1998.
(51) Int. Cl.$^7$ .................. G01N 33/53; G01N 33/543
(52) U.S. Cl. .................. 435/7.1; 435/7.92; 435/7.93; 435/DIG. 1; 435/DIG. 2; 435/DIG. 14; 435/DIG. 40; 435/DIG. 41; 436/518
(58) Field of Search .................. 435/7.1, 7.9, 7.92, 435/7.93, DIG. 1, DIG. 2, DIG. 14, DIG. 40, DIG. 41; 436/518, 501, 800, 543, 547, 548, 809, 546; 530/387.1, 808, 809; 935/110

(56) References Cited

U.S. PATENT DOCUMENTS

| | | | |
|---|---|---|---|
| 5,202,231 A | 4/1993 | Drmanac et al. .............. 435/6 |
| 5,326,692 A | 7/1994 | Brinkley et al. ............... 435/6 |
| 5,356,784 A | * 10/1994 | Kauver ...................... 435/7.9 |
| 5,525,464 A | 6/1996 | Drmanac et al. .............. 435/6 |
| 5,541,070 A | * 7/1996 | Kauver ...................... 435/7.9 |
| 5,573,909 A | 11/1996 | Singer et al. ................. 435/6 |
| 5,716,855 A | 2/1998 | Lerner et al. ............... 436/533 |
| 5,721,099 A | 2/1998 | Still et al. .................... 435/6 |
| 5,723,218 A | 3/1998 | Haugland et al. ........... 428/402 |
| 5,981,180 A | 11/1999 | Chandler et al. .............. 435/6 |
| 6,023,540 A | 2/2000 | Walt et al. .................. 385/12 |

FOREIGN PATENT DOCUMENTS

| | | | |
|---|---|---|---|
| EP | 0 577 092 | 1/1994 | |
| WO | 94/08051 | * 4/1994 | ............ C12Q/1/68 |
| WO | WO 95 28640 | 10/1995 | |
| WO | 95/32425 | * 11/1995 | .......... G01N/33/53 |
| WO | WO 97 14028 | 4/1997 | |
| WO | WO 99 19515 | 4/1999 | |

OTHER PUBLICATIONS

Keij et al., "Flow Cytometric Characterization and Classification of Multiple Dual–Color Fluorescent Microspheres Using Fluorescence Lifetime," Cytometry (1998) 33(3):318–323.
Waggoner, A., "Multiparameter Fluorescence Imaging Microscopy: Reagents and Instruments", Human Pathology (1996) 27:494–502.

Speel, E.J., "Sensitive Multicolor Fluorescence In Situ Hybridization Using Catalyzed Reporter Deposition (CARD) Amplification", J Histochem Cytochem (1997) 45:1439–1446.
Morrison, L.E., "Two–Color Ratio–Coding of Chromosome Targets in Fluorescence in Situ Hybridization: Quantitative Analysis and Reproducibility", Cytometry (1997) 27:314–326.
Urata, Y., "A Three–Dimensional Structure Dissection of Drosophila Polytene Chromosomes", J Cell Miol (1995) 131:279–295.
Paddy, M.R., "Time–resolved, in vivo studies of mitotic spindle formation and nuclear lamina breakdown in Drosophila early embryos", J Cell Sci (1996) 109:591–607.
Chen, H., "IVE (Image Visualization Environment): A Software Platform for All Three–Dimensional Microscopy Applications" J Structural Biol (1996) 116:56–6–0.
Kam, Z., "Three–dimensional microscopy in thick biological samples: a fresh approach for adjusting focus and correcting spherical aberration", BioImaging (1997) 5:40–49.
Swedlow, J.R., "Deconvolution in Optical Microscopy", Deconvolution of Images in Spectra, Second Edition, (1997), Academic Press pp. 286–307.
Kirk, G., "Quantitative X–ray imaging of labelled molecules in tissues and cells", J. Microscopy (1996) 183:181–186.
Borchardt, A., "Small molecule–dependent genetic selection in stochastic nanodroplets as a means of detecting protein–ligand interactions on a large scale", Chem and Biol (1997) 4:961–968.
You, A.J., et al., "A miniaturized arrayed assay format for detecting small molecule–protein interactions in cells", Chem and Biol (1997) 969–975.
Vorgt, R.F., "Model System Evaluating Fluorescein–Labeled Microbeads as Internal Standards to Calibrate Fluorescence Intensity on Flow Cytometers", Cytometry (1989) 10:294–302.
Beverloo, H.B., et al., "Preparation and Microscopic Visualization of Multicolor Luminescent Immunophosphors", Cytometry (1992) 13:561–570.
Napolitano, E.W., et al., "Glubodies: randomized libraries of gultathione transferase enzymes", Chem & Biol (1996) 3:359–367.

* cited by examiner

Primary Examiner—Padmashri Ponnaluri
(74) Attorney, Agent, or Firm—Morrison & Foerster LLP (57) ABSTRACT

Particulate labels that can be individually identified comprise particulate supports to which are bound at least two distinguishable signal-generating moieties, such as fluorophores emitting at different wavelengths, which signals are detectable and measurable in situ. By varying the ratio and/or amounts of the signal-generating moieties, a multiplicity of different and distinguishable labels is obtained. Each different label can then be coupled to a different reagent and the individual interactions of each reagent with a target observed in parallel.

12 Claims, 7 Drawing Sheets

METHOD TO ASSESS LIBRARY X LIBRARY INTERACTIONS

This application is a continuation-in-part of U.S. Ser. No. 09/146,984 filed Sep. 3, 1998 and incorporated herein by reference.

TECHNICAL FIELD

The invention relates to assay methods which utilize unique labeling particles containing signal-generating moieties whose ratio can be adjusted. More specifically, the invention concerns particulate labels wherein the hue of the label can be adjusted incrementally.

BACKGROUND ART

It is often desirable to test a sample for reactivity against a multiplicity of reagents. For example, in tissue typing, the ability of cells in a particular tissue to immunoreact with a panel of antibodies raised with respect to marker antigens is required. Genetic testing often involves detecting the polymorphic form of a particular gene by assessing its hybridization to only one of many allelic possibilities. There are also techniques for sequencing by DNA hybridization performed by probing immobilized reference spots of simple sequence DNA with the fragment to be sequenced. In this technique, the ratios of binding of the fragment to be sequenced to each of the simple sequences is unique for each possible sequence in the target fragment. Proteins generated from cDNA libraries representing characteristic expression products of particular cells can be screened for reactivity with various targets. The targets may include antibodies, for example, or small molecule drug candidates.

In all of these cases, either repetitious multiple testing with a variety of reagents is necessary, or the reagents are displayed in an orderly array, such as on a microtiter plate or on a "chip" to assess the reactivity of a sample. In all of these procedures, the association of a particular label with formation of a complex by binding to a component of the sample requires identification of the label by its position in time (for sequential testing) or space (for testing against a panel) or by further measurements on the label, that require its release from the solid particles, e.g., by mass spectroscopy. For example, U.S. Pat. No. 5,721,099 describes solid supports used in multistage synthesis of combinatorial libraries. Labels attached to the solid support identify the structure of the member of the library attached. The reaction history of each particle can be determined by the release of the label and analysis to determine the nature and amount of the tag.

It would be advantageous if a sample could be simply assessed for its reactivity with a multiplicity of reagents without the necessity for physical or temporal separation. The present invention achieves this result by employing labels whose identity can be assessed in situ by their degree of "gray," i.e., a property that can vary by small gradations between extremes over a wide range such as "white" to "black." While visible light is used as an illustration and as a means for explanation for simplicity herein, the invention includes embodiments of "color" which comprise other spectral properties such as radio frequency associated vibrational relaxation times in response to a magnetic field. Any property that can be varied over a wide range, as described above, can be employed. Thus, the nature of the label that is bound to a component of the sample is determinable by direct observation, enabling multiple parallel assays.

Attempts at multicolor labeling in a single sample have been made, most notably in "painting" chromosomes with labels of different color, a technique known as fluorescent in situ hybridization (FISH) with different colored labels for each chromosome. This technique has also been used to paint cells with different surface receptors by using binding ligands bearing different fluorophores. A summary of such approaches is set forth in Waggoner, A. et al., *Human Pathology* (1996) 27:494–502. The ability of the human eye to distinguish hues created by mixtures of different color components (although not with varied ratios of the same mixture of components) was demonstrated by Speel, E. J., et al., *J Histochem Cytochem* (1997) 45:1439–1446. Adaptation of this approach to oligonucleotide labels wherein dyes were applied at varying ratios to generate a number of different hues for the purpose of painting chromosomes was described by Morrison, L. E., et al., *Cytometry* (1997) 27:314–326. Although the labels are not particulate, and thus do not permit maximum signal intensity or the distinctive shape signal of uniform beads, this work does demonstrate that microscopic techniques can effectively detect and sort the hues generated when varying ratios of fluorophores are applied to a single label. As described in the catalog from Molecular Probes (Seattle), a microsphere of 100 nm diameter can be loaded with fluorescein to give an intensity equivalent to 7400 free fluorescein molecules with loading controllable to an accuracy better than plus or minus 5 percent.

The present invention offers the versatility of reagents and intensity of signal available through multihued beads wherein the particulate supports bearing signal-generating moieties are provided specific differentiable signals by virtue of these varying ratios. In addition, the labels can be evaluated not only in solution or suspension, but their location can be established through use of microscopic techniques in evaluating the samples.

DISCLOSURE OF THE INVENTION

Labels that can be identified by direct observation of their hue represent a great convenience in assays where multiple reactivities must be observed. The labels of the invention are particulate materials which contain at least two different signal-generating moieties—for example, each providing light of a particular wavelength range either by reflectance or fluorescence. Thus, in one embodiment, an individual particle will contain moieties that emit or reflect light of different colors. By adjusting the relative amounts of the different moieties attached to the particle, the perceived "hue" of the label will be different and it can be distinguished from other labels containing these moieties in different ratios. Effective use of these labels requires separate means for detection for each of the moieties coupled to the particle. Preferably, the particles contain at least three moieties which generate different wavelengths with a corresponding number of detection means.

Thus, in one aspect, the invention is directed to a label which comprises a particulate support to which is bound at least two signal-generating moieties, which moieties generate signals that can be distinguished in situ, such as light of different wavelengths. These labels are distinguishable by any instrumentation which contains separate means for detection for each of the at least two in situ signals generated. In general, separate detectors may be employed; however, a single detector may be employed using appropriate filters or other means, such as a prism or grating, to permit a single detector to perceive separately multiple signals, such as different wavelength ranges.

In particular, the in situ signals can be localized to obtain an overall pattern of labeling in a sample. Confocal optics and wide-field microscopy are able to distinguish structures on a microscopic scale and to permit observation of a geometric distribution of the labels of the invention.

In addition to establishing location of individual analytes on a microscopic level, the multihue particulate labels of the invention may be used macroscopically to map physiological phenomena. The labels can be used as "tracers" to follow endogenous pathways in complex systems. Thus, in another aspect, the invention is directed to a method to track physiological pathways by observing the distribution of the multihued labels of the invention, either as such, or provided with additional moieties showing an affinity for the pathway to be observed.

In another aspect, the invention is directed to an improved method for analyzing hue, or the ratio of signal-generating moieties on the multihued beads of the invention by observing the signals through wide-bandpass filters and correcting for the overlap.

In still another aspect, the invention is directed to a method to improve the definition of the hue associated with a particulate support by defining the observed signal in accordance with the known shape of the particulate support.

In another aspect, the invention is directed to a method to provide a desired ratio of signal-generating moieties on particulate support by coupling substantially all of the signal-generating moieties to be used to the support through linkers with differing lysis parameters. One embodiment of such linkers comprises short stretches of duplex DNA with the cleavage sites for different restriction enzymes for each different signal-generating moiety. For each single signal-generating moiety, more than one restriction site may be present. Alternatively, a single signal-generating moiety may be coupled through a multiplicity of linkers, each with a different cleavage parameter. Thus, a multiplicity of duplex DNAs would have different restriction enzyme sites. Under these conditions, the final ratio of signal-generating moieties can be controlled by varying the ratio of linkers used in fabricating the labeled particle and by the nature of the cleavage parameters used to treat the particulate.

In another aspect, the invention is directed to improved compositions of particulate supports which employ polymers that undergo phase transitions to open shapes such that the controlled variation in shape can be used to assist in adjusting the composition of labels on the particle.

In another aspect, the invention is directed to a collection of labels of the type described above wherein the ratio of the moieties differs from label to label in the collection. Typically, this collection of labels provides identifiable members that number at least twenty, preferably one hundred, more preferably five hundred, and still more preferably at least one thousand. Thus, if the reliability of detection of each color is plus or minus 10 percent, 10 gray labels exist for each signal and therefore 100 hues can be distinguished when two signal-generating moieties are included in each label. For use in analyzing a sample, each label will further be coupled to a different reagent.

In still another aspect, the invention is directed to a system for assessing the reactivity of a sample with a multiplicity of reagents coupled to labels, which system comprises the collection of labels bound to reagents described above along with separate detectors or their equivalents for the signals generated by each different moiety that is present on the particulates in the collection of labels.

Still another aspect of the invention relates to the use of collections of the labels in library versus library screening. Thus, for example, particles of different sizes may be associated with reagents that are potential opposite members of specific binding pairs such as antibodies/antigens where the antibody collection is bound to particulate supports of a different size as compared to the library of antigens. Successful binding can be detected by an aggregation of the smaller particles around the appropriately derivatized larger particle.

In still another aspect, particles of differing sizes can be used as a basis for homogeneous assays for analyte concentration in a competitive binding format or for affinity titrations by displacement of unlabeled analyte from larger particulates by competition from analyte analogs coupled to labeled, smaller beads.

In still another aspect, the invention is directed to methods of assessing the reactivity of components in a sample using the assay system described above.

MODES OF CARRYING OUT THE INVENTION

In a preferred embodiment, the labels of the present invention take advantage of the availability of detectors which can sense the intensity of light of particular wavelengths or wavelength ranges. Typical devices of this type are currently commercially available as charge coupled device (CCDs) equipped with standard color filters as used in camcorders for home videos. Higher sensitivity and reliability scientific grade CCD devices and filters are also available. A single CCD can be thus designed to detect only a narrow wavelength band of light, so that detectors can be obtained for, for example, red, green or blue light only. The CCD detectors are currently employed in wide field fluorescence microscopy, a technique which provides high resolution in three dimensions as well as time resolution. High precision instruments of this type are commercially available from Applied Precision (Seattle, Wash.) and are described in a series of papers authored by a group headed by John W. Sedat. These publications include Urata, Y., et al., *J Cell Miol* (1995) 131:279–295; Paddy, M. R., et al., *J Cell Sci* (1996) 109:591–607; Chen, H., et al., *J Structural Biol* (1996) 116:56–60; Kam, Z., et al., *BioImaging* (1997) 5:40–49. A summary of these techniques is provided in a chapter by Swedlow, J. R., et al., in "Deconvolution of Images in Spectra", Second Edition, (1997) Academic Press, pages 286–307.

This instrumentation provides fluorescence excitation and capacity for detection of three separate wavelengths of light. In current applications, these instruments can be and are used to detect the reaction of components in a sample with three different reactants each coupled to a latex bead having a color corresponding to one of the CCD detectors. Such beads are available commercially in several different colors of fluorophores with high uniformity in size and fluorophore doping levels from Flow Cytometry Standards Corp. (Puerto Rico); Molecular Probes (Seattle, Wash.); Polysciences (Warrington, Pa.); and from the Los Alamos LS-5 Cytometry Group, among others.

Figure 1:
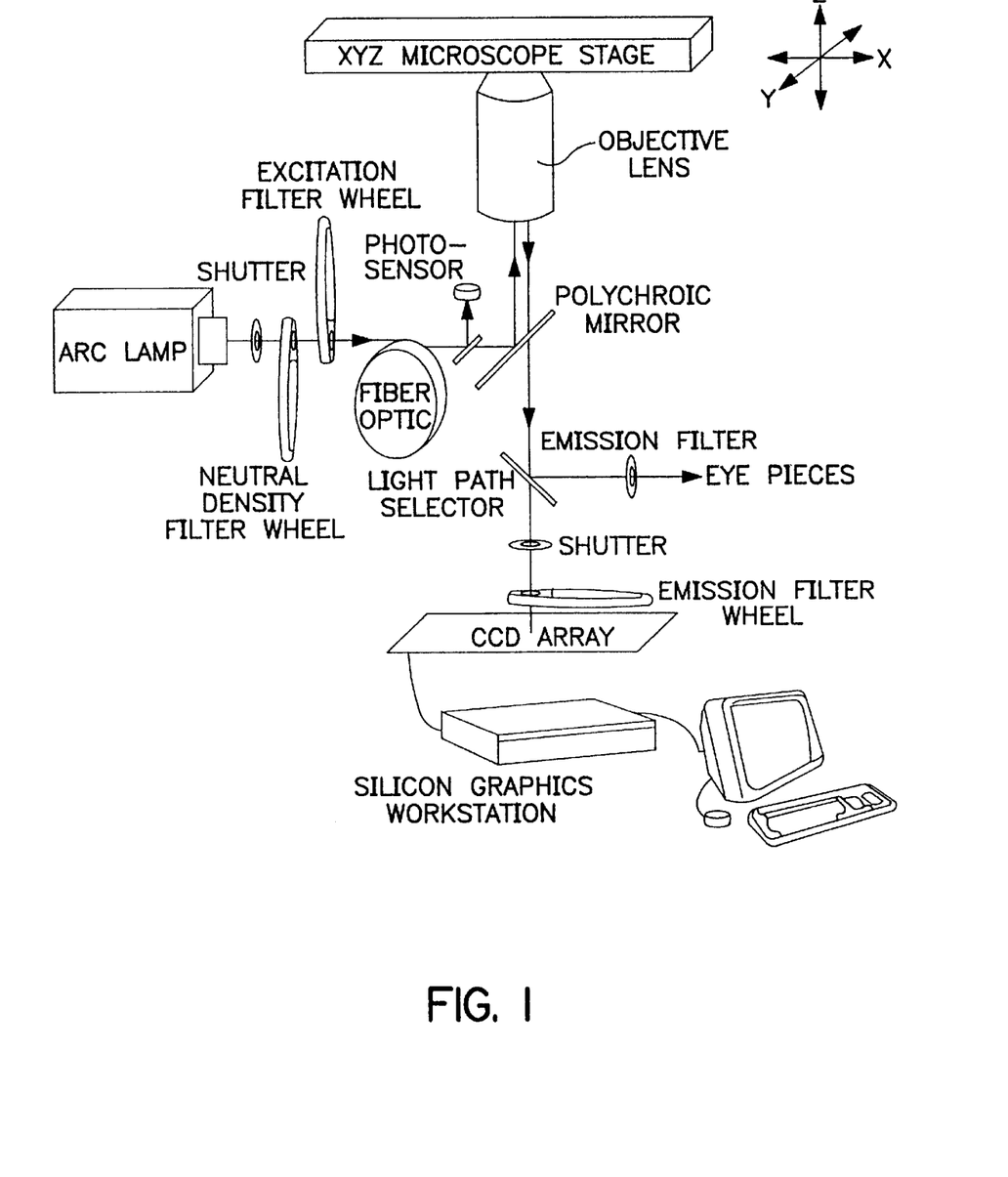
FIG. 1 is a diagrammatic representation of a system for detecting the label reactivity with a sample.

A schematic of a typical wide field fluorescence microscope with a single CCD detector and filter wheels is shown in FIG. 1. The multihued labels of the invention are conveniently read in this system. Fixed filters and separate CCD detectors, as diagramed in FIG. 3, simplify image registration and speed of data collection.

It will be apparent that one advantage of the detection devices employed in the invention that it is possible to locate the position of any specific particulate or group of particulates within the sample. Thus, the localization of a protein labeled with particulates containing a particular hue within a cell can be ascertained using the ability of the microscopic technique to produce a separate readout for each defined volume within the sample. Such an arrangement permits the observer to obtain a pattern of distribution for relevant analytes within the confines of a sample, such as within a Further, although it is advantageous to employ the high-grade narrow wavelength band CCDs and filters described above in discriminating the hues in the collection of particulates, an additional aspect of the invention renders this unnecessary.

A method for dealing with the distortions caused by broad wavelength bandpass filters is described in U.S. Pat. No. 5,834,203. As set forth in the '203 patent, an algorithm is applied to calculate the true signal associated with each color light by taking account of the known overlap contributed by dyes of different colors. Thus, if there are three dyes, red, green and blue which supply light to the various detectors, the detected signal in, for example, the red channel will be the sum of each dye concentration times its overlap. (For this purpose, the response to red itself is designated an overlap.) Thus, the signal in the red channel $S_R$ would equal the sum of each $O_R$, (overlap in the red channel for dye, d) $d_i \text{x}[d_i]$ or in different terms:

$$S_R = O_{R,R} \text{x}[R] + O_{R,G} \text{x}[G] + O_{R,B} \text{x}[B].$$

$$S_G = O_{G,R} \text{x}[R] + O_{G,G} \text{x}[G] + O_{G,B} \text{x}[B];$$

and $$S_B = O_{B,R} \text{x}[R] + O_{B,G} \text{x}[G] + O_{B,B} \text{x}[B].$$

As seen, this provides n equations in n unknowns.

The '203 patent would thus apply the algorithm to the detected signals (S) plugging in the known overlaps (O) and thus calculating the concentrations of the various dyes, which then defines the category.

Figure 4A:
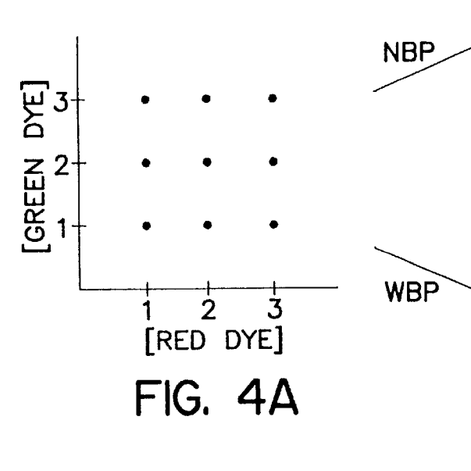
FIG. 4 shows the correction of color intensity when various dyes are measured using wide bandpass filters or detectors.
Figure 4B:
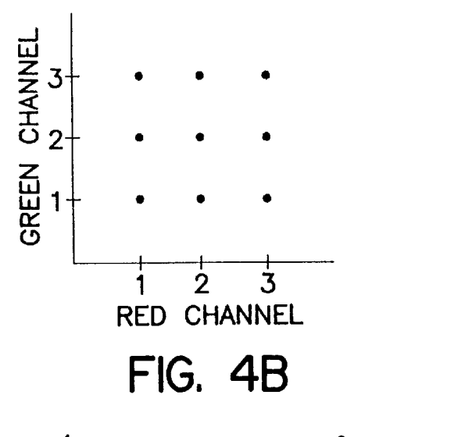
Figure 4C:
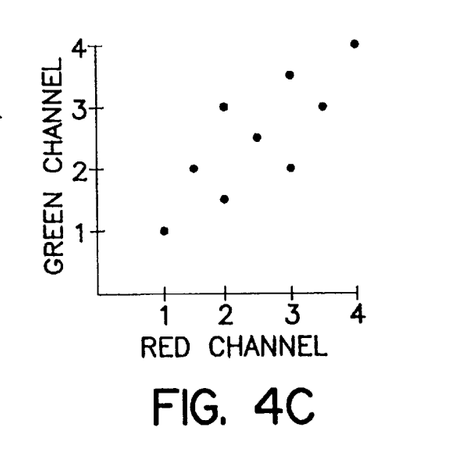
Figure 4D:
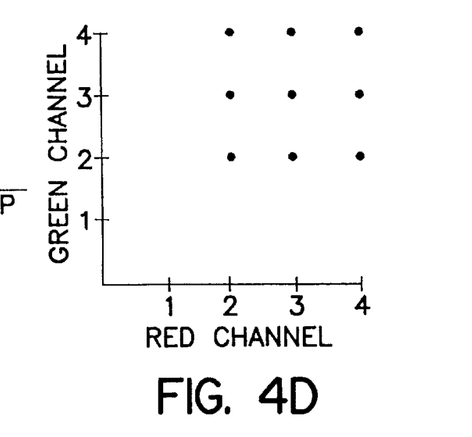
Figure 4E:
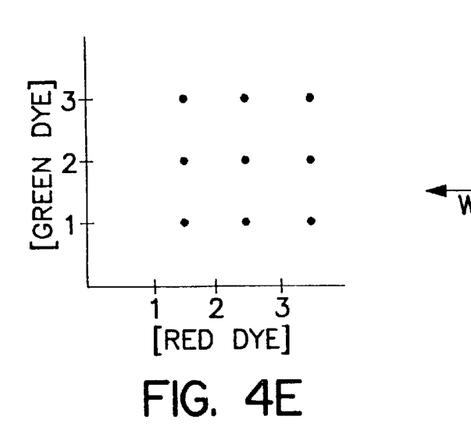

According to the improved method of the invention, however, account is taken of the overlap in generating the detected signal so that the ratio of category is directly obtainable from the output signals. FIG. 4 shows a diagram of the method used by the present invention to obtain the simple readout illustrated in FIG. 2 while using wider bandpass detectors which contain some overlap. As shown in FIG. 4A, categories can be defined based on presence of 1, 2 or 3 units of red or green dyes. The readouts obtained using detectors which faithfully record only light of the designated wavelength (i.e., a narrow band pass detector) are shown reflected in FIG. 4B. The intensity outputs from these devices faithfully record the actual intensities proportional to concentration from the relevant observed support. However, as shown in FIG. 4C, the outputs are distorted by the overlap when a wide band pass filter is used (i.e., where there is overlap into the red channel by the green dye and vice versa, illustrated here assuming each overlaps by 33% into the other's primary detection channel). For example, a category defined as 2:2 (red:green dye) gives an output observed in the red channel of 2.6. The algorithm in the '203 patent is intended to convert the observed intensities back into dye concentrations, which form the basis of a classification. Alternatively and more simply, according to the method of the present invention, the inputs are adjusted to take the overlap into account. Thus, categories defined by observing the simple pattern shown in FIG. 4D are created by adjusting the inputs as shown in FIG. 4E. A category defined by observing 3:3 (red:green), for example, is created by adding 2.25 units of each of red and green dyes to the particle. Back calculation on the observed signals is thus no longer needed.

The Multihued Labels

The present invention multiplies the number of reagents that can be separately detected under these conditions by systematic and precise doping of particulate supports with signal-generating moieties, typically fluorophores, of different colors corresponding to the CCD detectors employed, at specified ratios. Particles with different ratios of the fluorophores generate different detection signals in this system. Because the ratios of the fluorophores can be varied at will, up to a point where a forced proximity of the dyes leads to quenching, many different "hues" can be generated in a collection of labeled particles, each particle type having a unique ratio and/or amount of color generating moieties. If each different label is coupled to a different reagent, the collection can be used to run multiple assays at once as each particle can be identified by the hue of the light it generates.

As used herein, the term "label" is generally used to describe a particulate support to which has been bound an appropriate array of signal-generating moieties. The signal-generating moieties must be such that the signals are detected in situ on the particulate support. Thus, it is unnecessary to detach the signal-generating moieties from the support in order to ascertain their ratio. Their ratio is read directly by means of the "hue" of the label. Color is a preferred signal. The labels of the invention contain at least two, and preferably at least three, distinguishable signal-generating moieties. The ratios and amounts of the signal-generating moieties provide each label with a particular "hue"—i.e., a particular combination (ratio and absolute intensity) of the at least two and preferably at least three signal-generating moieties. When used, the label will be coupled to a "reagent"—i.e., a substance associated with the label to detect a complementary analyte. For use in the convenient assays of the invention, a collection of labeled reagents will be required—i.e., a "multi-hue array"—a set of labeled reagents for which the hue corresponding to each reagent is well defined.

As visible light is a particularly convenient way to generate a particular "hue," this embodiment of the invention is exemplified herein. However, other signal-generating moieties can be employed or an indirect method to generate visible light may be used. For example, particles may be provided with radioisotopes having different energies along with insoluble scintillants. $^3H$ and $^{35}S$ contained in a single particle with insoluble scintillants give distinguishable photon bursts, as is the basis for pulse height analyzers used in standard scintillation counters. Alkaline phosphatase and horseradish peroxidase contained at specific ratios with appropriate substrates provide different signals, including those generated by chromophores or, more directly, different electrochemical reducing powers. In addition, heavy atom clusters of different materials, for example colloidal gold dots versus ferrite rods offer different scattering characteristics with respect to electron microscope beams. Kirk, G., et al., *J. Microscopy* (1996) 183:181–186. The preferred "color generating" moieties are typically fluorophores, but they can also generate a characteristic wavelength either by reflectance (simple dyes) or by emission (fluorophores or de novo light-generating compounds such as a luciferase or other chemiluminescent system). A number of chemiluminescent systems are known in the art such as horseradish peroxidase-based generation of chemiluminescent products. Suitable absorbing dyes include alizarin red, thiazole yellow, naphthyl green Y, indophenol blue, and Gentian violet. Suitable fluorophores include dansyl, green fluorescent protein, fluorescein, Hoechst, Texas Red, merocyanines, and the like. A number of dyes covering a wide range of wavelength emissions have been developed as described in Waggoner, A. et al., *Human Pathology* (1996) 27:494–502, incorporated herein by reference. In addition to fluorescent dyes, phosphorescent materials (such as lanthanide metal chelates) may also be employed which adds the advantage that time resolved fluorescence distinguishes signals that would be equivalent averaged over a longer detection period. Light emitting systems which do not require excitation by external radiation include the combination of radioisotope and scintillant embodiment set forth above as well as the enzyme systems that generate distinguishable chromophores or act on spontaneously chemiluminescent substrates.

Conceptually, simply varying the ratio offluorophores is the most straight-forward way to alter hue. However, more sophisticated approaches include selecting the dyes so that they interact in predetermined ways, for example by energy transfer wherein excitation at the excitation maximum for a first dye results in a non-radiative transfer to a second dye which then emits. Different input ratios with respect to the excitation peaks of the two dyes result in different outputs under the appropriate conditions. Further, if one dye is placed on the interior of the particle and the other on the exterior, a hue will be created that is distinct from that obtained when the two dyes are mixed uniformly throughout the particle, or when the positions of the dyes are reversed.

The supporting particles are typically 0.1–1 $\mu$m in diameter and are preferably latex. However, smaller particles may also be used. Generally, 50 nm (0.05 $\mu$m) is considered an approximate minimum; it has been possible in some contexts to use particles as large as 5 $\mu$m, although this is not preferred. The use of larger particles results in lower diffusion rates and thus, effectively, less efficient and less vivid labeling. A preferred range is 100–500, preferably 100–300, and more preferably 100–200 nm diameter particles. The particulate supports are generally spherical, and the microscopic techniques employed can distinguish spherical shapes from other general outlines. However, other particulates may also be used, such as polyvinyl, polysaccharides such as dextran and sepharose, polymers such as cross-linked polyacrylamide and polyethylene glycol and the like. Silica gel particles may also be used. Any particulate that has suitable physical properties (does not spontaneously aggregate, adhere, or otherwise fail to behave as an independent particle) and which can be suitably derivatized with the color generating moieties and with the test reagent may be used.

The construction of the particle itself affects the hue detected. In addition to differences attributed to the size of the particle, as indicated above, the shape will determine the nature of the signal. Shapes can vary along the continuum of sphere to oval to rod to string, for example. Star shapes or other arbitrarily shaped particles can be created by x-ray lithography so as to have a distinctive point spread function. Thus, any aspect of the labeled particle that provides a distinctive signature can be used. As an example, a refractive index is affected by the density and composition of the particle itself. In short, two particles with the same ratio and absolute intensity of fluorophores but distinguishable shapes have distinctive hues as defined herein.

In addition to the information component contributed by the shape of the particle, knowledge of the particle shape can be used to enhance the signal-to-noise ratio. Since the detectors survey the particle over space, the ratio is improved by examining the observed output channel intensity only across the volume of space defined by the known shape and size of the particulate support. Pixels which fall outside the defined shape are rejected as noise, thus sharpening the image of the particle.

A preferred method to filter such data is to collect a three-dimensional array and apply Fourier transform techniques to recognize the underlying shape despite any distortions in its directly observed form. That is, the observed image is the convolution of the actual signal and the point spread function of the lens. Deconvolution in the Fourier representation is advantageous since it replaces difficult computations with simpler arithmetic. Further, since effective magnification differs slightly for different wavelengths, a SIMLEX algoritm is useful to align images observed in each of several channels using landmarks spread across spatial dimensions of the sample. Particulate supports of known size are particularly convenient landmarks.

For particles several times larger than the wavelength of the light used, distortions in output represent only a few percent of the size of the object, but for smaller particles, the distortions are more substantial.

Finally, notwithstanding the desirable characteristic listed above that the particles useful in the invention do not aggregate, controlled aggregation may be employed in appropriate instances to obtain size variance based on the proportions of the constituent particles. For example, if the particles are derivatized with bifinctional or monofunctional cross linkers, different ratios of bi and mono linkers in mixtures of particles will lead to aggregates of different sizes. This approach may be particularly attractive in in vivo applications wherein small particles, even individual dye molecules, are more readily transported into cells. These can then be designed to self assemble into particulates by virtue of enzymatic activity or by photolysis.

The nature of the coupling techniques for both the color generating moieties and the reagent will depend on the nature of the supporting particle, the nature of the color generating moiety, and the nature of the reagent. Suitable linking techniques are well known in the art. By way of example only, if the reagents are proteins, they may be recombinantly produced with a hexahistidine sequence or with an epitope, such as a FLAG epitope which can then be bound to particles which are manufactured to incorporate a nickel chelator or an antibody to the epitope. Standard linking techniques applicable to a multiplicity of substances and to the functional groups available on particulate supports include disulfide linkages generated from sulfhydryl moieties on each component and amide linkages generated from carboxyl and amino functional groups. Other examples include homobifinctional and heterobifinctional linkers as set forth in the catalog for Pierce Chemical Company, Rockford, Ill.

Additionally, techniques which employ subtraction methods are feasible based on techniques described by Shreiber (Borchardt, A., et al., *Chem and Biol* (1997) 4:961–968; You, A. J., et al., ibid. 969–975) both incorporated herein by reference. Shreiber showed that graded amounts of a ligand can be released from a bead by photolysis of a labile bond wherein a mixture of signal-generating moieties can be used initially, and a certain portion of them selectively subtracted. As described by Shreiber, the initial coupling is through a bond labile to light; by light exposure, photolysis occurs and a portion of the signal-generating moiety is released.

As applied to the present invention, the signal-generating moieties can be coupled to the particulate support through linkers having different requirements for cleavage, so that the linkers which attach a red dye, for example, could be selectively cleaved as opposed to those which couple the particulate to a green dye. One exemplary approach to such differential cleavage comprises the use of duplex DNA containing one or more restriction sites. By treating the particulate support with different restriction enzymes, particular signal-generating moieties can be selectively removed. In addition, a single signal-generating moiety may be coupled to the bead by a defined set of linkers, each cleaved in a different manner so that the ratio of linkers used in fabricating the particulate supports is also a factor in determining the hue.

For example, a red dye might be coupled to the particulate through a DNA containing a restriction site for EcoRI, a green dye through a DNA with a restriction site for BamHI, and a blue dye with a DNA with a restriction site for XbaI. A defined amount of green dye could be removed by treating the particulate support with BamHI, leaving the red and blue coupled dyes intact. Alternatively, the green dye could be attached as a mixture, some of the green dye coupled through DNA containing a BamHI site and another portion attached to the DNA containing a SmaI site. Treatment with SmaI, then, would remove only a portion of the green dye. Techniques for coupling the duplex DNA both to the dyes and to polymer supports are well known.

This method can be refined by plating out a collection of the beads all containing a multiplicity of signal-generating moieties coupled differentially to the beads and overlaying the collection with a grid containing differing release reagents at different locations, thus assuring that each location will have removed a different proportion of each signal-generating moiety. Alternatively, the dyes and their DNA linkers can be immobilized as a reservoir from which different amounts of each dye can be released depending on the pattern of releasing enzyme used. The resulting dyes released from the reservoir can be passively incorporated into beads growing at that location by accretion of polymer. Whether the DNA cleavages occur on the bead or the reservoir, the result is the same. A spatial pattern of beads corresponds to a hue pattern. Accordingly, the spatial pattern can be matched to a spatial pattern of e.g., antibodies.

Rather than a covalent attachment of the reagent to label, the reagent may simply be physically associated with it, for example by being trapped in a thin layer of agar coating the particulate label. The reagent is released when the sample to be analyzed is contacted with a collection of labels by melting the agar. The polymers described in U.S. Pat. No. 5,783,302 have advantages over agar for coating beads. Because these polymers have a sharp transition temperature, adjustable over most of the range between 0° and 100° C., they can be transiently melted to imbibe compound, which is then fixed until release by another mild temperature pulse. In this way, any compound library can be handled analogously to the way combinatorial chemistry libraries are currently handled. The physical proximity of the label then serves to identify the reagent that reacts successfully with a component of the sample. Such an approach exploiting physical proximity was described by Borchardt, A., et al., *Chem and Biol* (1997) 4:961–968; You, A. J., et al., ibid. 969–975. These documents also describe photolabile linkers and use of an aerosol generator to create droplets comprising coated beads.

As stated above, the manner of construction of the labels depends on the nature of the signal-generating moiety and the chemical composition of the solid support. One exemplary procedure is set forth in Vogt, R. F., et al., *Cytometry* (1989) 10:294–302 which describes a linear relationship between moles of FITC added to latex beads and integrated intensity of fluorescence observed in a cell sorter. Using the techniques there described, a wide multiplicity of hues can be obtained by varying the amounts of each signal-generating moiety.

In contrast to the present invention, the description of preparing colloidal particles each carrying a single inorganic phosphor, as set forth in Beverloo, H. B., et al., *Cytometry* (1992) 13:561–570, emphasizes that the particles labeled with individual reagents should be supplied sequentially to the sample rather than as a mixture. Sequential supply is needed in order to provide an unambiguous picture since the ratio of antigens determines the ratio of captured antibody. On the other hand, the labeled reagents of the present invention may readily be supplied to the sample as a mixture as they are readily distinguished by the different hues of their labels examined individually.

Figure 2:
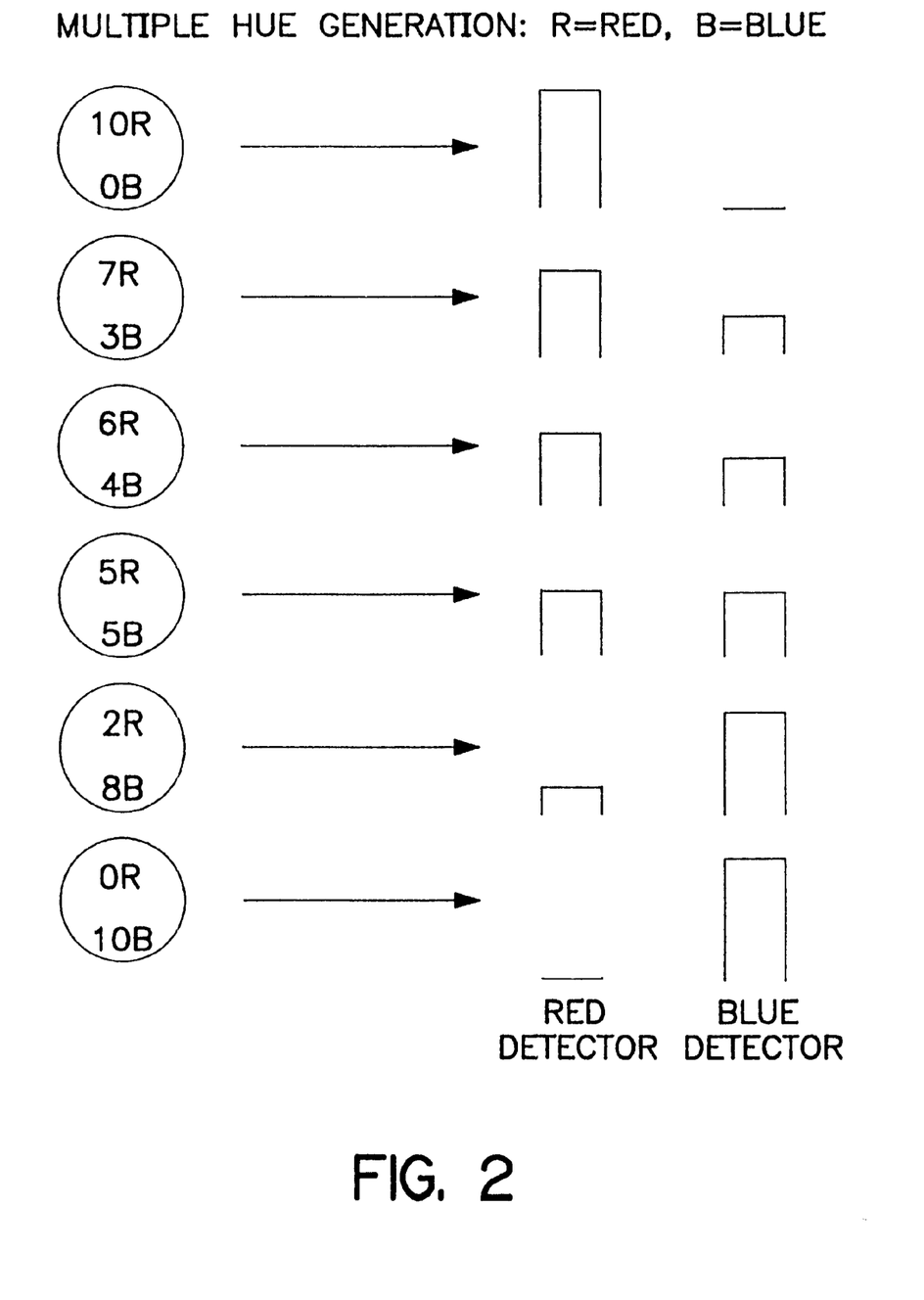
FIG. 2 diagrams the composition of a representative sample of labels of varying colors.

Each label, then, will contain at least two different signal-generating moieties, typically fluorophores, and for use in assays will be coupled to the relevant reagent. Each different reagent will be coupled to a different label. The invention method for generating a multiplicity of different labels is illustrated in FIG. 2 for beads with only two fluorophores. In this illustration, the ratio of the red light generating moiety to blue light generating moiety is varied over a series of ten levels for each color. This results in a hundred different "hues"—i.e., ratios and intensities. As shown in FIG. 2, different signals will be obtained depending on the ratio and/or amount of red and blue color generating moieties. The ratios and intensities of the responses in the red and blue detectors is indicative of the label being measured. Since the detectors can measure intensity as well as color per se, labels which contain a ratio of 10 red to 2 blue can be distinguished from labels that contain 5 red to 1 blue. An additional multiplier of the number of different possible labels can be added by varying the size of the particulate support which can be independently measured in the microscope system described above.

Similar extensions can be made with additional colors of fluorophore in multiple dimensions. The multiplicity of colors available is limited only by the availability of suitable discrimination capabilities with respect to light generation and detection. Thus, if three color generating moieties are included, each of which can be reliably classified into ten shades of gray, labels with 1,000 different hues can be generated. If each color generating moiety can be reliably classified into 100 levels of gray, 1 million different hues are enabled for a collection of these labels.

Uses of the Multihued Labels

Most of the applications of the multihued labels of the invention involve coupling of the labels to reagents specific for a binding pair member. However; the multihued labels have applications which do not necessitate the use of such reagents. Generally, the labels may be used to elucidate physiological pathways, especially in instances where a complex array of pathways is overlapping.

The general principle is that where such pathways exist, they can be followed by permitting the labels to travel their course. For example, the connections of nerve endings in the spinal cord to their origin in the brain track microtubule "rails" that transport organelles up and down the axon. The particles of the invention preferably less than 200 nm in diameter, more preferably less than 50 nm diameter, can be caused to penetrate into the nerve endings, "riding the rails" so to speak into the origin of the axon. The mechanism whereby the particulate supports will be taken up by the nerve endings is not completely understood; it is believed that receptor-mediated endocytosis simply engulfs the particulate by mistake. This phenomenon of retrograde transport has been widely used in neuroanatomy. The retrograde transport of the particulate support can then be observed directly. Conversely, anterograde transport from the nerve cell body to axons and dendrites is also observable through the use of particulate labels of the invention, although getting the particulate labels into the cell is generally not as easy. By using a multiplicity of hues, a multiplicity of such pathways can be observed. In addition, the migration of cells of a particular type in a developing embryo could also be followed.

Figure 5:
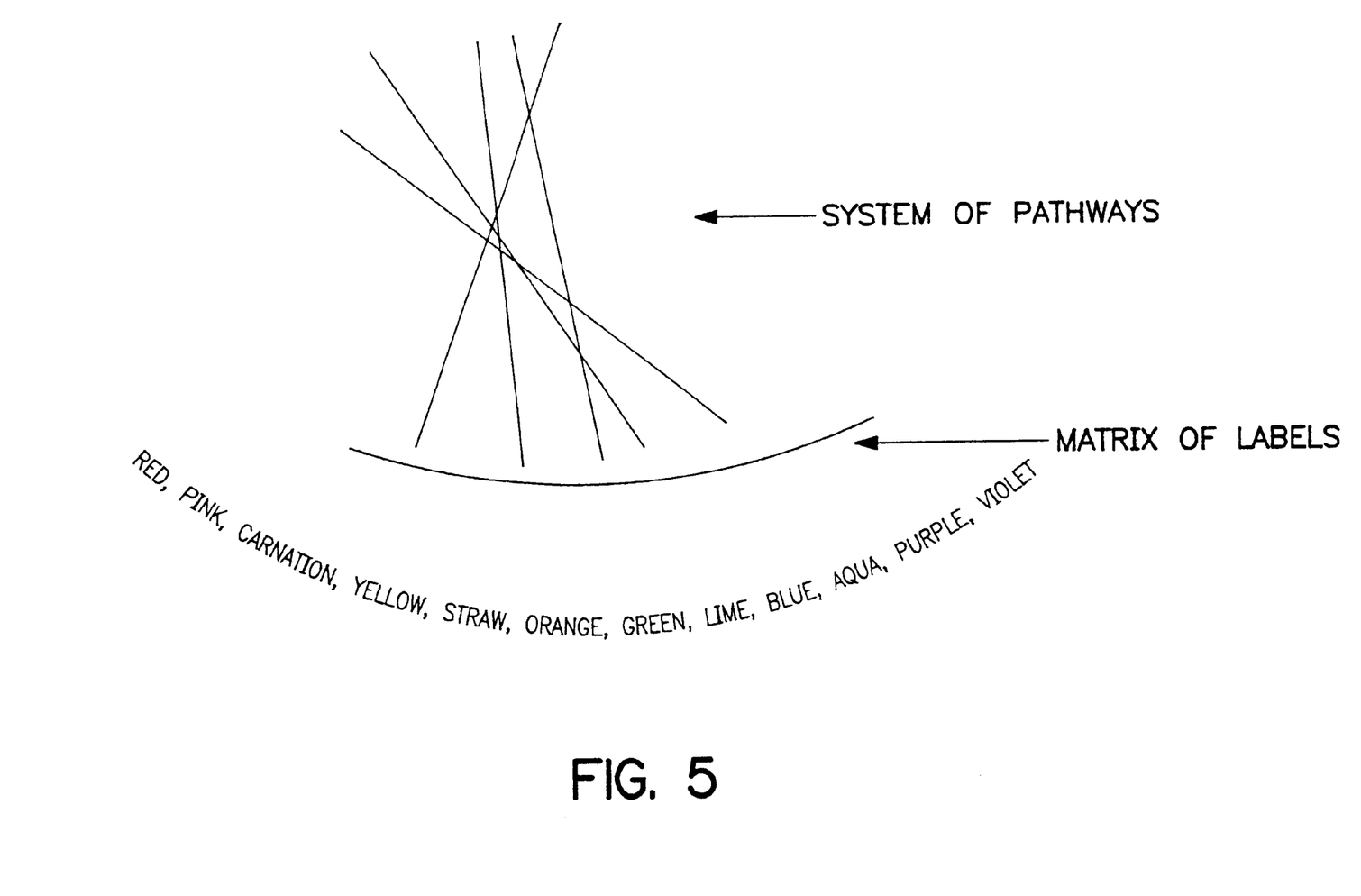
FIG. 5 shows the observation of complex pathways using a defined matrix of label.

In order to organize the observations in following physiological pathways, it is often helpful to apply the multihue labels systematically across the field of cell or dendrites. This is illustrated in FIG. 5 which shows how a defined matrix of multihued beads can be used to sort out overlapping pathways. Since a multiplicity of beads is absorbed by each pathway endpoint, a similar result could be achieved by providing a matrix with locations containing various combinations of single-color beads; i.e., the difference in hues is achieved by varying the bead mix rather than by varying the mix on an individual bead. However, it is more convenient to take advantage of the variety of colors obtainable by mixing primary colors in varying ratios on a single particulate support.

For use, generally, the labels are attached to reagents so that each individually hued label is coupled to a different known reagent. The nature of the reagent can then be ascertained from the hue of the label to which it is attached. The reagent will be any substance or compound that is reactive with a potential target or analyte. Suitable reagents, then, include proteins, carbohydrates, nucleic acids, including oligonucleotides, and the like, depending on the nature of the assay that is to be run.

One particularly useful set of reagents comprises a class of proteins typically known as "antibodies." This class offers the generation of a large variety of binding regions of varying specificities. The classical "antibody" specific for a particular antigen is obtained through immunization of a suitable vertebrate and recovery of polyclonal antibodies from the plasma or serum or recovery of monoclonal antibodies through hybridoma technology. It is well known that antibodies as obtained in this way are not required in their entirety for binding specificity; only the variable regions need be present. Thus, included within the term "antibodies" as used herein, are fragments of the antibodies such as $F_{ab}$, $F_{ab'}$, and $F_{(ab')_2}$ fragments. In addition, the availability of recombinant techniques makes possible altered and species-adapted forms of specifically binding regions, such as single-chain $F_v$ "antibodies." More generally, "antibodies" is used herein to refer to any group of proteinaceous compounds which can contain a variable binding region. Thus, the solvent-exposed loop present in many proteins can be altered in structure using mutagenic techniques to afford a wide variety of binding specificities. Napolitano, E. W., et al., *Chem & Biol* (1996) 3:359–367. In addition, peptides and other oligomers with a wide variety of specificities can be constructed using combinatorial techniques to obtain panels of paralogs with widely differing binding specificities. Kauvar, L. M., U.S. Pat. No. 5,340,474 (1994), As used herein, "antibodies" includes all such variably binding proteins.

In addition to proteins, nucleic acids, in particular oligomers, can be widely varied in binding specificity. A number of techniques are available for generating oligomers of differing binding specificities; e.g., the Selex technique (U.S. Pat. No. 5,567,588).

Of course, the nature of the reagent depends on the nature of the application. Antibodies are useful in tissue-typing and other diagnostic assays, peptides generated from cDNA libraries are useful in-assessing receptor binding, for example. Reagents which are oligonucleotides are useful in assays based complementary chain hybridization. Reagents that are combinatorial chemistry library members are useful in screeing for medicaments. The choice of reagent depending on the purpose and type of assay is well within ordinay skill in the art.

Thus, the multihued labels of the invention are useful in a variety of assays, especially those where multiple reactivities must be assessed. One example, as noted above, is tissue typing where standard serology defines major types and subtypes. The labels coupled to diagnostic antibodies may be designed for example so that larger beads, each having three fluorophores at different ratios are coupled to different antibodies representing major classes, thus permitting the identification of up to one thousand major classes. Similarly, small beads each having three fluorophores can distinguish among one thousand subtypes. Thus, in theory, a single tissue specimen could be classified with regard to a million sera. As a practical matter, however, only about one thousand separate antibodies would be needed to do an adequate classification.

In this, and in other applications, it will be necessary to fix tissue to be tested. Standard fixation conditions which include, for example, glutaraldehyde are less favored since it is desirable to provide permeable surfaces for the labels of the invention. Variation of the fixation conditions, further, may result in discrimination among labels of different types, which adds another dimension of distinguishability. Polymers particularly useful for fixing tissue samples under these circumstances are typified by those manufactured by Landec (Palo Alto, Calif.) which exhibit sharp transitions between gel and sol states over a given temperature range. The differences in transition temperatures between these polymers are achieved by varying derivatization, such as hydroxylation. Fixing the sample is achieved by infiltrating the tissue with a polymer at above its transition temperature—i.e., in the sol state, and then fixing for sectioning by cooling. By varying the proportions of the polymers with different transition temperatures, the degree of permeability can be regulated in the resulting sample, generally by rewarming after sectioning. Further temperature manipulations can vary the permeability as desired.

In another application, a cDNA library is tested for proteins that interact with a target by producing a multiplicity of beads each with a different "hue" i.e., ratio of color generating moieties and/or different intensity of color generation and each with a different protein from the library. This set of multihued beads can then be tested all at once for binding to a particular target, and the successful interaction identified by the signal generated of the bead to which it is attached. The target may be an immobilized natural product or receptor; alternatively, this system may be adapted to detect interaction between two libraries of proteins or two collections of substances generally, in an analogy to the yeast two hybrid assay.

The assay system characterized by the labels of the invention can also be adapted for use in nucleotide sequencing by DNA hybridization, as described in U.S. Pat. Nos. 5,202,231 and 5,525,464. In this adaptation, each reference simple DNA sequence is attached to a different label. The collection of labeled sequences is then applied to multiple copies of the fragment to be sequenced. Typically, the fragment is immobilized and probed with the collection of labels.

Figure 3:
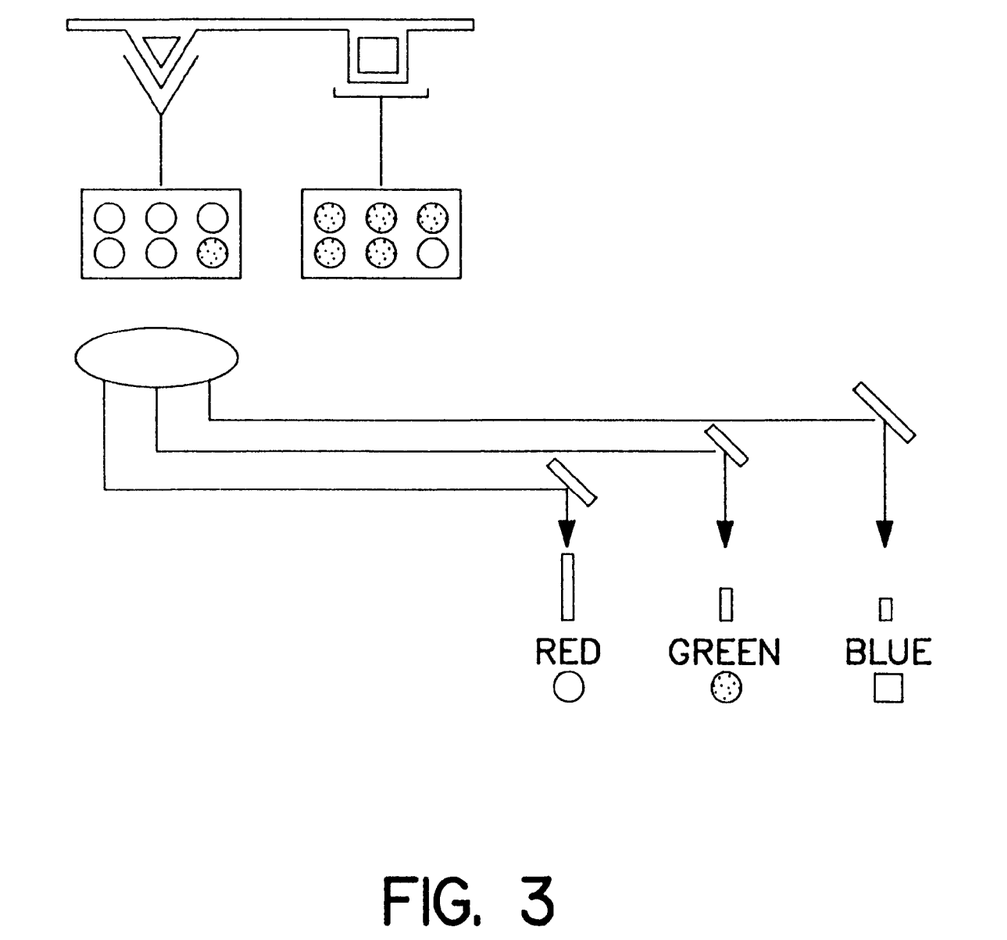
FIG. 3 diagrams an assay system for analyzing a solution for a multiplicity of analytes in which each reagent with its corresponding label is imaged independently.

The collection of labels, each coupled to a different nucleotide sequence, can also be used in genetic testing. In one design, larger particulates, for example, contain long nucleotide sequences complementary to conserved regions of the gene and are used to define whole genes under stringent hybridization conditions whereas another set of smaller particulate based labels containing shorter nucleotide sequences may be used to detect mutations in regions of polymorphism under hybridization conditions where even a single mismatch leads to reduction in signal. The labels may be read in a high precision wide field microscope with CCD detectors appropriate to the color generating moieties which comprise the label without the need of a washing step because the sharp focal plane of such instrumentation permits distinction between labeled sequences which are hybridized to surface-immobilized target and those which are not. Thus, samples from a series of time points, for example, can be concurrently assayed for expression of many genes. Similarly, examination of gene expression in embryonic development, arrested at defined time points is possible, allowing spatial and temporal patterns of expression to be simply determined. FIG. 3 diagrams this approach schematically. The solid triangle and solid rectangle represent two analytes immobilized in the focal plane, for example, in a tissue slice. The presence of each analyte in the tissue slice is detected via the labels bearing reagents for each of these analytes.

Still another instance where analysis with respect to multiple reagents is desired is in the screening of combinatorial libraries. Each member of the combinatorial library is attached to a label with a different ratio and/or quantity of color generating moieties. Thus, the identity of the compound in the library which is capable of binding to target can be ascertained by the intensity and color generated by its label. The addition of the color generating moieties to the particulate label can be carried out in conjunction with the synthesis of the library members so that the amount or ratios of the color generating moieties are coordinated with the structural features of the library members. Alternatively, the color-generating moieties may be attached via labile linkers and different amounts of label removed by controlled degrees of photolysis or chemical cleavage.

One application of a combinatorial library is a library of recombinant antibodies having randomized binding sites. This library, with members coupled to labels of different ratios of color generating moieties and/or light intensities may be used to probe protein libraries, for example those obtained by expression of cDNAs which have been transferred to nitrocellulose.

To prepare such a library of labeled antibodies, a convenient approach is as follows:

The particulate supports, initially uniformly labeled with color generating moieties that are coupled to the particulates through linkages that are lysed by specific wavelength activation are spread over a surface. Filters can then be employed in a specific pattern over the surface so as to generate a multiplicity of ratios of the color generating moieties and of total amounts thereof. The result is a two-dimensional surface where the labels are varied in a systematic way. The surface is then overlain with individual colonies each producing a different recombinant antibody. Preferably, the antibodies are modified by hexahistidine or the FLAG epitope to make their linkage to the corresponding label more facile. The collection of antibodies labeled with the multihued array then can be pooled and used to screen a sample for antigens having reactivity with the these antibodies. Recovery of the cells producing the successful antibodies is accomplished by reading the hue of the label and referencing each to the two-dimensional surface pattern where that hue was created, and onto which the clones were deposited. In this way, antibodies specifically reactive with antigens expressed in situ can be identified for subsequent diagnostic uses.

Similar protocols may be used to determine specific interactions of proteins or peptide members of two different libraries containing nucleotide sequences in a manner analogous to the yeast-to-hybrid assay. The interaction of the two proteins can be modified by intermediate linkers so that the interaction of proteins in one library with small molecules, for example, in another, may also be assessed. Interaction between nucleotide sequences and proteins, such as enhancers and transcription factors, can also be elucidated in this way.

The protein members of the combinatorial library need not, of course, be antibodies but can, instead, be the products of a cDNA library. Thus, the labels and methods of the invention permit screening of cDNA×cDNA libraries, for example to identify specific antibody interacting proteins for nearly all genes identified by the human genome project. Matching DNA promoter sequences with transcription factors are similarly enabled as described above.

More generically, the methods of the invention can be used to assess secreted proteins in general. Cells which secrete these proteins are plated in two-dimensions and covered with a capture layer which includes, for example, DEAE-agarose combined with CM-agarose which together will bind most proteins. Alternatively, the capture layer may include an antibody or other specific binding pair member complementary to the secreted protein. The secreted and captured proteins can be tested against an array of labeled antibodies directed to epitopes on the captured proteins that remain exposed.

Another application relates to screening one library against another. As noted above, a library of antibodies could be screened against a library of antigens. The antibodies or antigens or both could be provided per se or generated from expression cDNA libraries or combinatorial nucleic acid libraries. To facilitate such library×library screening, it is useful to have the members of one of the libraries are coupled to particulate supports which are relatively larger than the supports used for coupling the members of the library presumed to contain the opposite members of the specific binding pairs to be matched. Interaction of the two sets of particulates will result in formation of "rosettes" of successful pairing where the pair member bound to the larger particulate acquires an accumulation of a number of the smaller particulates which contain the opposite member of the binding pair. The presence of the rosettes can be detected conveniently with a pattern filter, so that this is conducted as a homogeneous assay. The results of the determination of the interaction of the members of the first library and the members of the second library can be recorded in computer-readable form.

Figure 6:
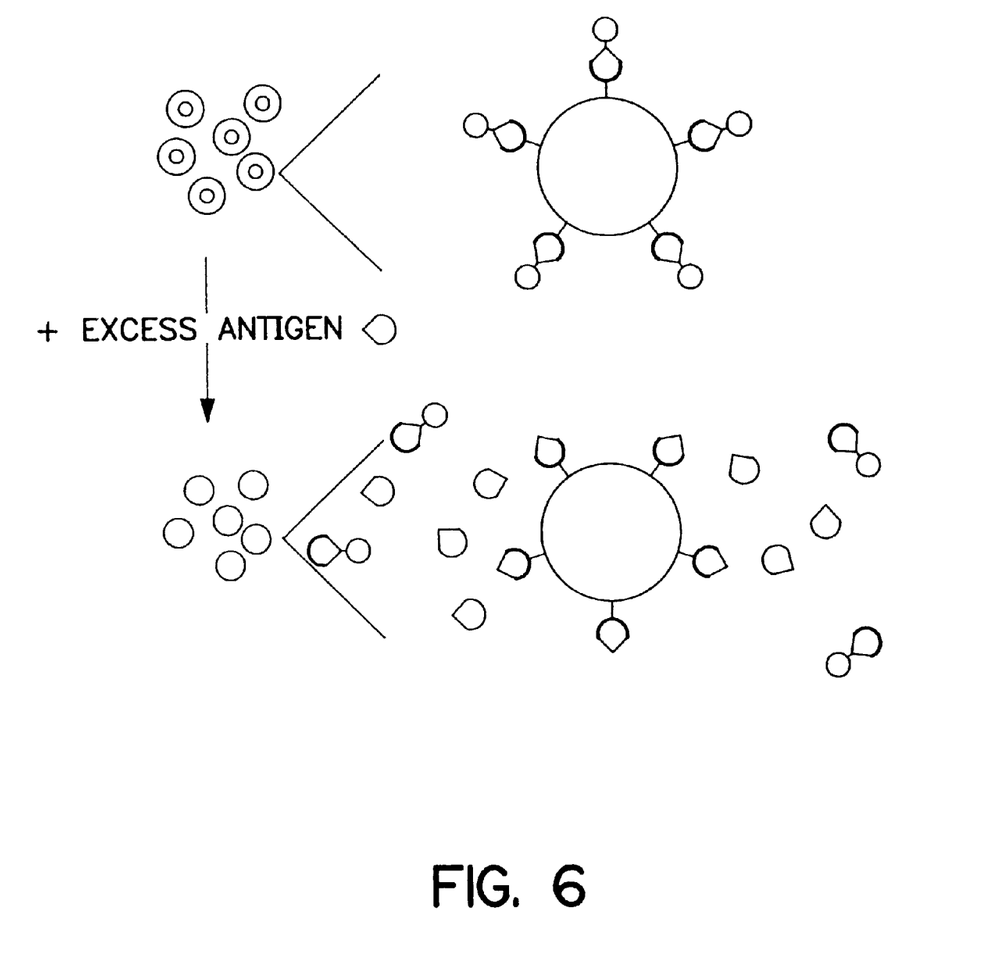
FIG. 6 shows the use of a rosette pattern as an end-point using competition assays.

The use of the rosette pattern as an end point can also be employed in assays for analyte concentration using competition assays wherein the analyte in a sample will compete with corresponding molecules bound to small particulate supports for an opposite member of the specific binding pair coupled to the large particulate support, as illustrated in FIG. 6. Higher concentrations of analyte result in more effective competition, thus diminishing the concentration of rosettes obtained. In addition, the affinity of the interaction that leads to the rosetting can be varied as set forth in U.S. Pat. Nos. 5,356,784 and 5,620,901, incorporated herein by reference. The competitive assays can be conducted in homogeneous format, thus making them suitable for intracellular concentration determinations. Thus, production of phosphotyrosine by receptor activation can be detected inside living cells using antibodies against this motif.

Figure 7:
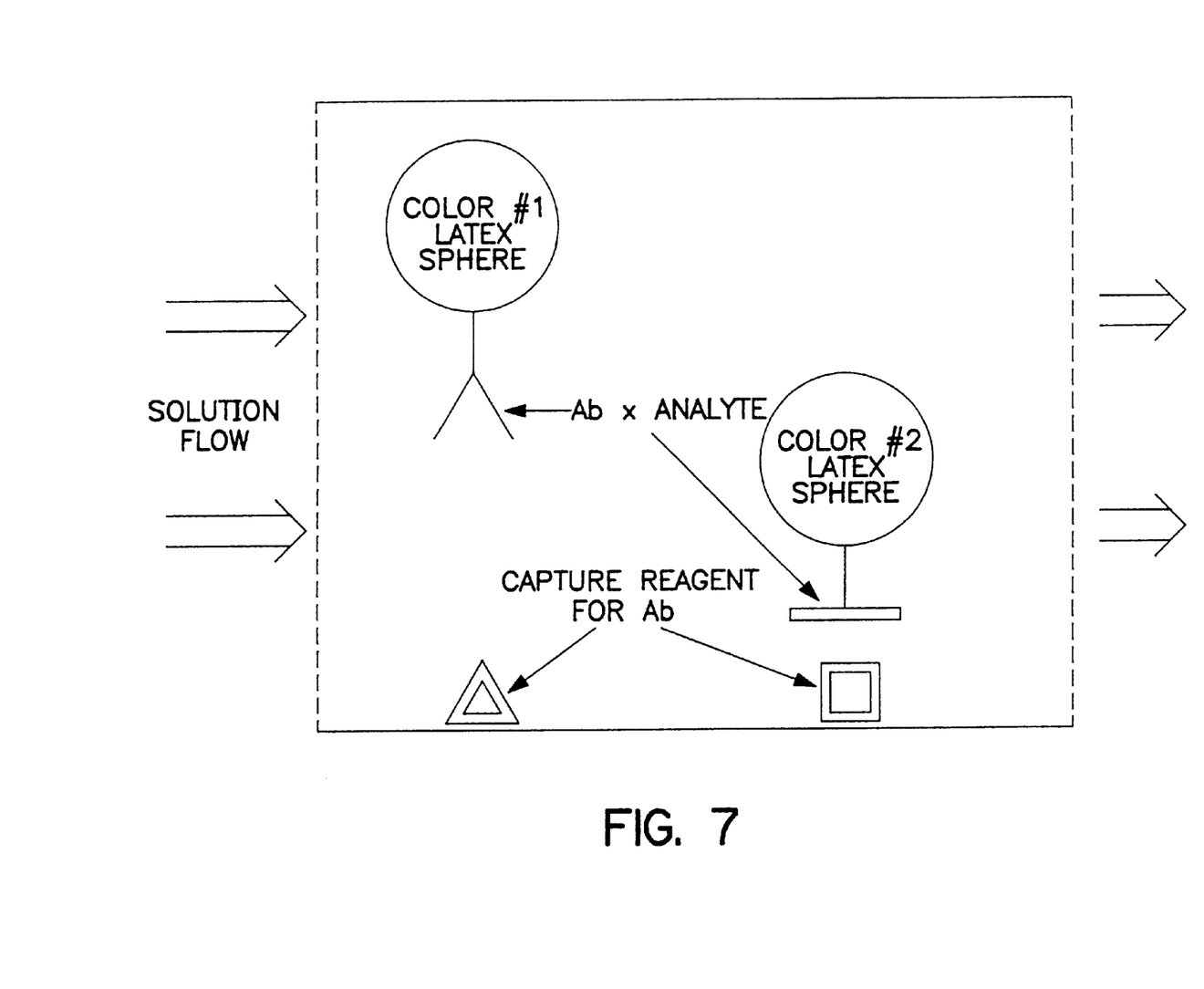
FIG. 7 diagrams a continuous operation biosensor.

Another specific application of the methods and materials of the invention relates to the use of a biosensor which can be designed for continuous analysis of an analyte solution. The analyte solution is passed through a mesh containing a collection of labeled reagents where the size of the mesh pores is too small to permit the labeled reagents to pass; thus, the labeled reagents are trapped within the sensor. The compartment defined by the mesh further contains competing analogs of the analyte contained in the solution in a position where label can be detected—i.e., for example, the focal plane of a microscope. Thus, the label is only perceived if it is captured by the competing analog of the analyte in the appropriate position. As the sample to be analyzed passes through the compartment defined by the mesh, any analyte in the sample competes for label with the analogs constrained to the focal plane, thus releasing label from the location in which it can be detected. A diminution in detectable label thus indicates the presence and amount of analyte in solution. As a collection of multihued labels can be used, a multiplicity of analytes can be assessed simultaneously. This is shown schematically in FIG. 7. Such a system is useful for continuously monitoring the levels of a drug and its metabolites in blood and urine, for example.

What is claimed is:

1. A method to assess the interaction of a first library of compounds with a second library containing, potentially, compounds which are opposite members of specific binding pairs which method comprises providing a first composition which comprises members of said first library of compounds wherein each of said compounds is coupled to a particulate label having a hue different from that of the particulate label to which any of the other members of said first library is coupled;

providing a composition comprising members of said second library of compounds wherein each of said compounds is coupled to a particulate label having a hue different from that of the particulate label to which any of the other members of said second library is coupled; and wherein the particulate labels in said first library are sufficiently larger in size so that the labels in the second library form rosettes with respect to labels in the first library;

contacting first composition with said second composition wherein binding of a compound from the first library to a compound of the second library, if any, results in a rosette which consists essentially of a first particulate label to which the compound of the first library is bound surrounded by a multiplicity of second particulate labels to which said compound of the second library is bound; and observing the formation of any said rosette;

wherein said observing is by employing a microscope;

wherein the formation of said rosette demonstrates that said second library contains at least one compound that is the opposite member of a specific binding pair of a compound of said first library;

and wherein the hue of each particulate label is generated by binding to a particulate support at least two signal generating moieties in predetermined amount and ratio, each of which moieties generates, in situ, a signal different from that generated by the other moiety(ies) bound to the same particulate support such that each combination of said signals provides a hue characteristic of said label.

2. The method of claim 1 which further includes the step of recording, for each possible interaction between any compound which is a member of the first library with any compound which is a member of the second library, the formation or nonformation of a rosette to obtain recorded data and storing said recorded data in computer-readable form.

3. The method of claim 1 wherein the members of the first library are proteins and the second library is a combinatorial library.

4. The method of claim 1 wherein the members of the first library are antigens and the members of the second library are antibodies or fragments thereof.

5. The method of claim 1, wherein the first library is a combinatorial library and the members of the second library are receptors.

6. The method of claim 1, wherein the members of the first library are potential ligands and the members of the second library are receptors.

7. The method of claim 1 which further comprises identifying the hue of the first particulate label contained in any rosette and identifying the hue of the second particulate label contained in any rosette, thus identifying the member of the first library and the member of the second library which participate in the rosette.

8. The method of claim 1 wherein either of said first or second particulate labels are characterized by at least three signal generating moieties.

9. The method of claim 1 wherein said signal-generating moieties are color generating moieties.

10. The method of claim 9 wherein the color generating moieties are fluorophores.

11. The method of claim 1 wherein either of the supports comprising the first or second particulate lables are latex beads.

12. The method of claim 1 wherein the first particulate labels have diameters of about 100–500 nanometers and the second particulate lables have diameters of about 50 nm–100 nm.

* * * * *